United States Patent
Wang et al.

(10) Patent No.: US 8,244,336 B2
(45) Date of Patent: Aug. 14, 2012

(54) PORTABLE ELECTROCARDIOGRAPH

(75) Inventors: Weihu Wang, Beijing (CN); Lei Chen, Beijing (CN); Peng Wu, Beijing (CN)

(73) Assignee: Beijing Choice Electronic Technology Co., Ltd., Beijing (CN)

( * ) Notice: Subject to any disclaimer, the term of this patent is extended or adjusted under 35 U.S.C. 154(b) by 298 days.

(21) Appl. No.: 12/299,178

(22) PCT Filed: Feb. 8, 2007

(86) PCT No.: PCT/CN2007/000449
§ 371 (c)(1),
(2), (4) Date: May 8, 2009

(87) PCT Pub. No.: WO2008/061407
PCT Pub. Date: May 29, 2008

(65) Prior Publication Data
US 2009/0299206 A1    Dec. 3, 2009

(30) Foreign Application Priority Data
Nov. 24, 2006 (CN) .......................... 2006 1 0144947

(51) Int. Cl.
*A61B 3/12* (2006.01)
*A61B 5/02* (2006.01)
(52) U.S. Cl. .................. 600/509; 600/523; 600/508
(58) Field of Classification Search .................. 600/509, 600/523, 508
See application file for complete search history.

(56) References Cited

U.S. PATENT DOCUMENTS

| | | | | |
|---|---|---|---|---|
| 7,197,351 B2 * | 3/2007 | Umeda et al. | ................. | 600/393 |
| 7,310,550 B2 * | 12/2007 | Ishida et al. | ................. | 600/523 |
| 7,489,359 B2 * | 2/2009 | Fukumoto et al. | ............ | 348/360 |
| 7,515,963 B2 * | 4/2009 | Axelrod et al. | ................. | 607/32 |
| 2006/0047210 A1 * | 3/2006 | Moroki et al. | ................. | 600/509 |

FOREIGN PATENT DOCUMENTS
CN    1636507 A    7/2005
CN    1739446 A    3/2006

* cited by examiner

*Primary Examiner* — Niketa Patel
*Assistant Examiner* — William Levicky
(74) *Attorney, Agent, or Firm* — Seyfarth Shaw LLP; John C. Serio

(57) ABSTRACT

A portable electrocardiograph, in which an exposed electrode is arranged on the end face of one end of a housing, characterized in that: the other end of the housing is of a comfortable structure for holding; the comfortable structure for holding is provided with the other exposed electrode; and the geometric center of the comfortable structure for holding is of an offset toward the other end of the housing and one of the two transverse sides, and a measuring key is arranged in the geometric center of the comfortable structure for holding. The present invention is of a humanized and unique holding structure shape, which ensures the wrist, the arm, and the trunk of the user are closed to form a relative space, thus allowing the user to measure in natural and correct posture so as to make sure the monitored data to be accurate and reliable.

9 Claims, 4 Drawing Sheets

PORTABLE ELECTROCARDIOGRAPH

TECHNICAL FIELD

The present invention relates to a portable electrocardiograph, in particular to a portable electrocardiograph which can ensure correct using posture so as to accurately monitor electrocardiogram waveform and data.

BACKGROUND OF THE INVENTION

At present, the electrocardiogram of patient needs to be measured in monitoring and diagnosis of arrhythmia.

The patent publications CN1739446A and CN1636507A disclose a portable electrocardiograph, in which patient can measure his/her own heart state by oneself at any time and any location, monitor the electrocardiogram waveform in real-time, and store the monitored data, thereby being greatly convenient for monitoring demands of patient. However, there also exist deficiencies.

As shown in FIGS. 1 and 2, the portable electrocardiograph is provided with two exposed electrodes. The user holds one exposed electrode of the electrocardiograph by right hand during measurement, and makes the other exposed electrode of the electrocardiograph contact the left chest. Since the electrocardiograph is shaped into a straight-plate cuboid, the first two knuckles of a finger can round one corner of the cuboid and reach the position of contacting electrode when the user holds the electrocardiograph to contact the left chest thereof, while the finger's knuckle connecting the palm substantially maintains parallel to human body during the measurement. Thus, the wrist of the right hand is naturally to press close to the straight-plate cuboid. In addition, lower arm and large arm are involuntarily to press close to trunk part of upper body, thus making the distance L to be smaller, even make direct contact of the right hand and the right rib abdomen, resulting in the measuring circuit in this part to be in short circuit. If it were in this case, the measuring circuit could not pass across the heart, therefore the electrocardiogram waveform and data cannot be measured in high precision.

In addition, since the electrocardiograph is of straight-plate cuboid shape, the arm muscle is to be in more nervous state if the posture of the user is unnatural during measurement. At this moment, the electrocardiogram waveform is subjected to larger myoelectricity interference, so as to cause the distortion of electrocardio signal.

The basic reason causing the above deficiencies is that in the prior art the portable electrocardiograph is of a cuboid shape, such that the user is uneasy to be in the correct posture of measurement when holding the electrocardiograph.

SUMMARY OF THE INVENTION

The object of the present invention is to provide a portable electrocardiograph, in which the accuracy of electrocardio measurement can be greatly improved, and the errors in measured waveform and data caused by inaccurate posture of user can be effectively prevented.

The further object of the present invention is to provide a portable electrocardiograph, in which every man can accurately monitor the electrocardiogram waveform and data by oneself.

For this purpose, according to the present invention, a portable electrocardiograph is provided, in which an exposed electrode is arranged in the end face of one end of a housing. The portable electrocardiograph is characterized in that the other end of the housing is of a comfortable structure for holding; the comfortable structure for holding is provided with the other exposed electrode; and the geometric center of the comfortable structure for holding is arranged to be offset toward the other end of the housing and one of the two transverse sides, wherein a measuring key is arranged in the geometric center of the comfortable structure for holding.

Preferably, the comfortable structure for holding is a more than half circular body with a circular arc shape.

Preferably, a power supply key is arranged on the side of the housing, and a combined key for controlling, displaying, and storing is arranged on the side of the housing.

Preferably, one end of the housing is of a rectangular, a trapezoid, a drum, or a square shape.

Preferably, the transverse side of the housing is the right side.

Preferably, the transverse side of the housing is the left side.

Preferably, a display screen is arranged on one end of the housing.

Preferably, the radius of the arc end of the more than half circular body is in the range of 20 to 100 mm.

Preferably, with respect to the geometric center of one end of the housing, the arc end of the more than half circular body is with a longitudinal offset distance from 10 to 100 mm.

Preferably, with respect to the geometric center of one end of the housing, the arc end of the more than half circular body is with a transverse offset distance from 25 to 100 mm.

According to the present invention, since the housing of the portable electrocardiograph is of a humanized and unique holding shape, the wrist, the arm, and the trunk of the user are structurally enclosed to form a relative space, thus allowing the user to measure in natural and correct posture. Therefore, the measured data is accurate and reliable, thereby greatly improving the accuracy of electrocardio measurement, and effectively preventing the error in measured waveform and data due to inaccurate posture of the user.

Meanwhile, according to the present invention, the wrist of the user is uplifted naturally when the user performs measurement. The arm is in a more natural posture, thus, the muscle is not nervous, thereby greatly reducing influence on the electrocardio signal from the myoelectricity interference, and therefore reducing the distortion of electrocardio signal.

DETAILED DESCRIPTION OF THE PREFERRED EMBODIMENTS

Next, the embodiments of the present invention are described in more detail in combination with accompanying figures.

As shown in FIGS. 3 to 8, the portable electrocardiograph according to the present invention comprises a housing, a built-in power supply, and a built-in detection and control circuit.

Figure 1:
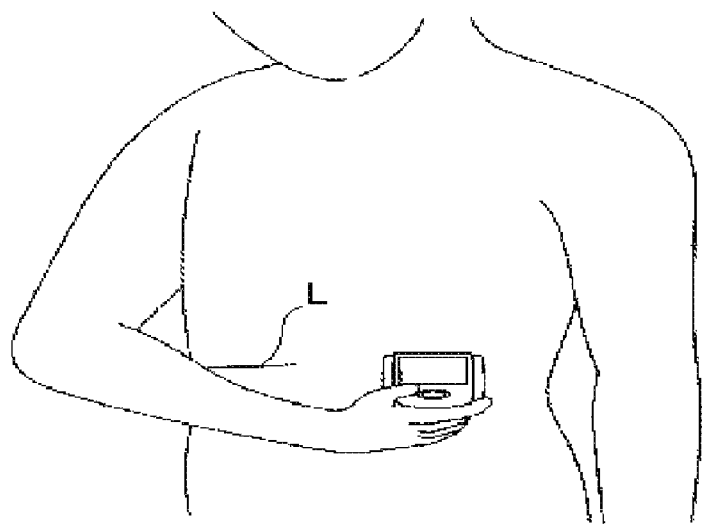
FIG. 1 is a front view of measurement posture for holding the portable electrocardiograph according to the prior art.
Figure 2:
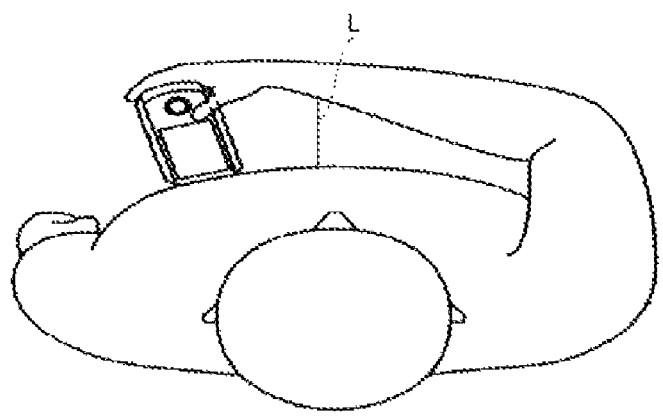
FIG. 2 is a plan view of measurement posture for holding the portable electrocardiograph according to the prior art.
Figure 3:
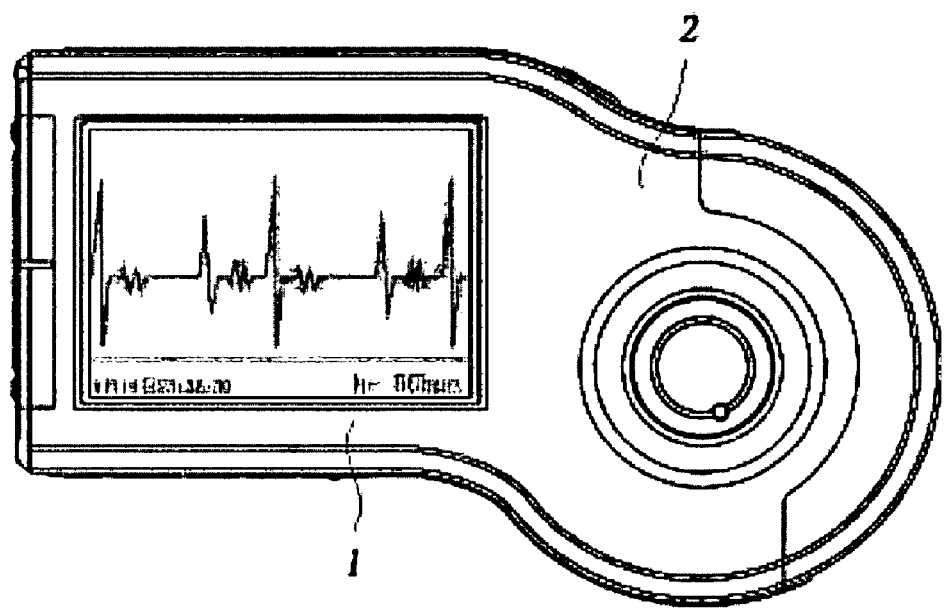
FIG. 3 is a main view of the portable electrocardiograph according to the present invention.
Figure 4:
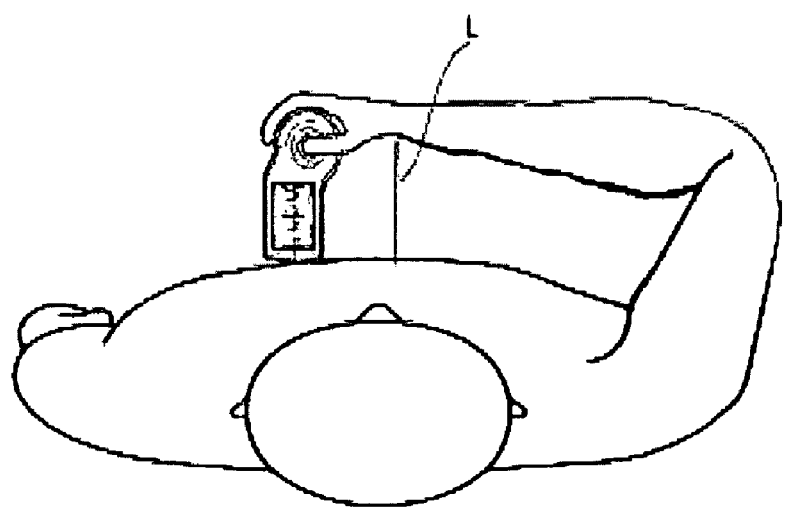
FIG. 4 is a plan view of measurement posture for holding the portable electrocardiograph according to the present invention.
Figure 5:
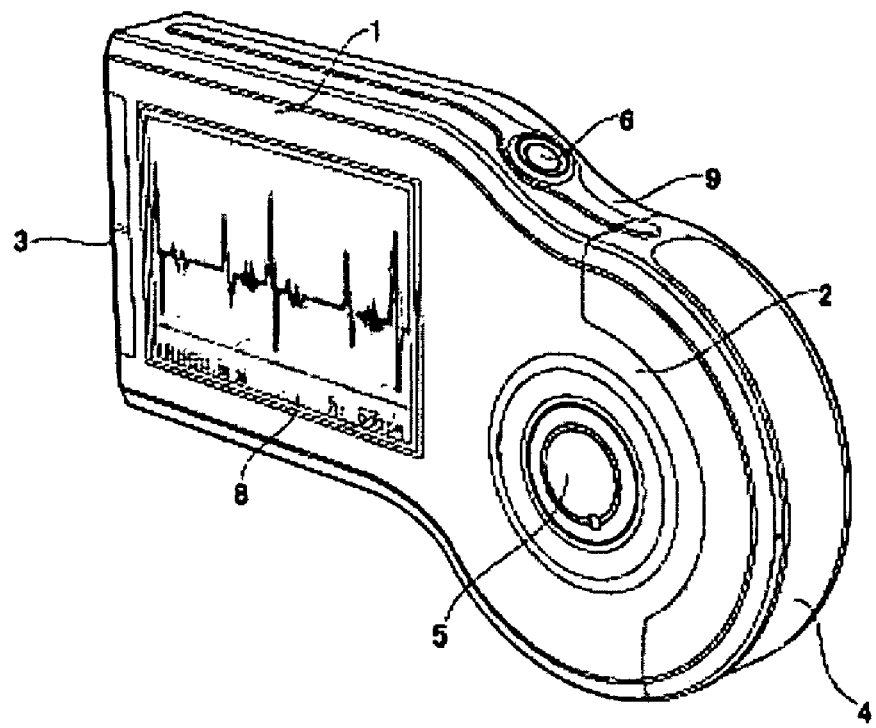
FIGS. 5 to 8 are perspective views of the portable electrocardiograph according to the present invention when observed from different visual angles.
Figure 6:
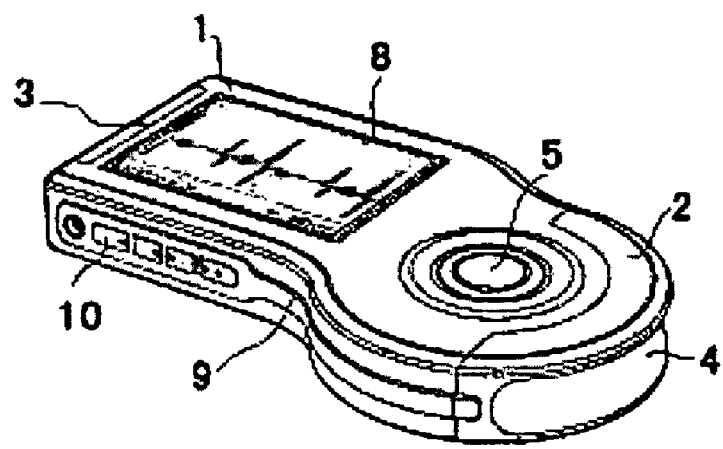
Figure 7:
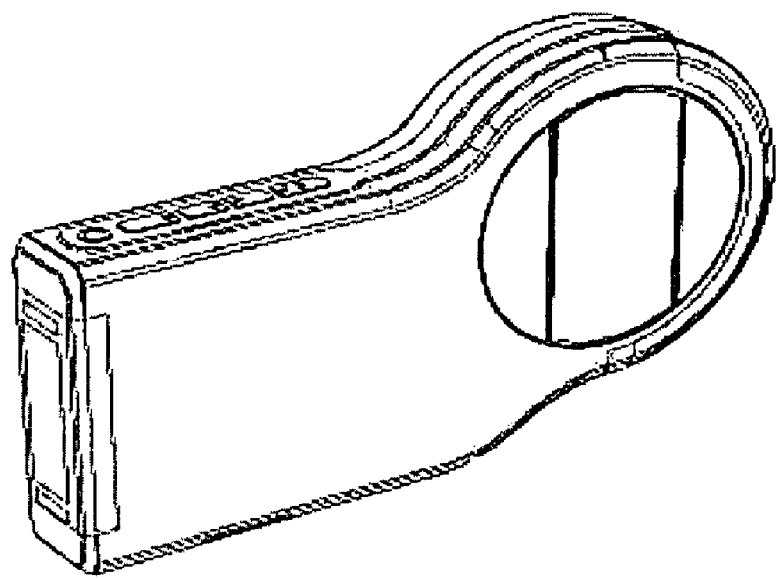
Figure 8:

As shown in FIG. 5, the left end of the housing is a cuboid 1, and an exposed electrode 3 is arranged on the end face thereof. A display screen 8 is arranged on the front surface of the cuboid 1. The right end of the housing is a more than half circular body 2 having approximately three-quarter arc shape structure, and the other exposed electrode 4 is arranged in the arc thereof. The circle center of the more than half circular body 2 is arranged in a position below the right side of the vertical central axis of the cuboid 1. A measuring key 5 is arranged in the circle center of the more than half circular body 2. A power supply key 6 is arranged in the connecting portion 9 between the cuboid 1 and the arc circle of the more than half circular body. As shown in FIG. 6, a combined key 10 for controlling, displaying, and storing is arranged on one side of the cuboid 1.

To start the measurement, the user presses down the power supply key 6. Then, the more than half circular body 2 of the housing of the electrocardiograph according to the present invention is held by the right hand, and the forefinger of the right hand is operated to press on the electrode 4 in the arc of the more than half circular body 2 and maintain to contact reliably. The thumb of the right hand is operated to place on the key 5. The electrode 3 on one end of the cuboid 1 of the housing of the electrocardiograph according to the present invention is operated to contact the heart position in left chest. The thumb of the right hand presses down the measuring key 5 during measurement, and then the display screen 8 can display the measured waveform. At the same time, the operation of controlling and storing key 10 can also be performed so as to store the monitored waveform and data for future reference.

Since the right hand holding portion of the user is with a structure of the more than half circular body 2 and the holding part is arranged in the position below the right side of the vertical central line of the cuboid 1, the wrist position of the right hand becomes higher when the user holds it, and the large arm and lower arm of the right hand naturally extends outward, thus the wrist, the arm, and the trunk of the user are closed so as to form a relative space. Such a posture is natural for the user without any uncomfortable feeling, meantime, the correct measuring posture is ensured, such that the object of accurate measurement is achieved. The user can perform measurement in natural and accurate measuring posture, and the monitored data is accurate and reliable, thereby greatly improving the accuracy of electrocardio measurement, and effectively preventing from the error in measured waveform and data caused by inaccurate posture of the user.

According to other embodiments of the portable electrocardiograph, the more than half circular body having arc shape structure on the other end of the housing may also be replaced by other comfortable holding and humanized structures, for example, an ellipsoid having arc shape structure, or a curved surface shape with finger pad positioning dent or the like may be used.

According to other embodiments of the portable electrocardiograph, the cuboid shape of the housing may be replaced in trapezoid, drum shape, square, or other ornamental shapes.

The present invention is described above in detail according to a plurality of embodiments. However, those skilled in the art should understand that various modifications and improvements can be made on the present invention, while such modifications and improvements do not depart from the spirit of the present invention and scope of protection defined by the attached claims of the present invention.

The invention claimed is:

1. A portable electrocardiograph comprising, a housing with two transverse sides in which an exposed electrode is arranged on an end face of one end of said housing, wherein said other end of the housing is of a comfortable structure for holding said comfortable structure for holding is a more than half circular body having an arc shape structure, and is provided with another exposed electrode; a geometric center of said comfortable structure for holding is arranged to offset toward the other end of the housing and one of two transverse sides of the housing, and a measuring key is arranged in the geometric center of said comfortable structure for holding.

2. The portable electrocardiograph according to claim 1, characterized in that a power supply key is arranged on the side of the housing; and a combined key for controlling, displaying, and storing is arranged on the side of the housing.

3. The portable electrocardiograph according to claim 1, characterized in that said one end of the housing is in a shape of a rectangular, a trapezoid, a drum shape, or a square.

4. The portable electrocardiograph according to claim 1, characterized in that said one of the two transverse sides of the housing is the right side.

5. The portable electrocardiograph according to claim 1, characterized in that said one of the two transverse sides of the housing is the left side.

6. The portable electrocardiograph according to claim 1, characterized in that a display screen is arranged on said one end of the housing.

7. The portable electrocardiograph according to claim 1, characterized in that a radius of an arc end of the more than half circular body is in a range of 20 to 100 mm.

8. The portable electrocardiograph according to claim 1, characterized in that with respect to the geometric center of said one end of the housing, an arc end of the more than half circular body is of a longitudinal offset distance ranged from 10 to 100 mm.

9. The portable electrocardiograph according to claim 1, characterized in that with respect to the geometric center of said one end of the housing, an arc end of the more than half circular body is of a transverse offset distance ranged from 25 to 100 mm.

* * * * *